United States Patent [19]

Anderson

[11] Patent Number: 4,673,574

[45] Date of Patent: Jun. 16, 1987

[54] IMMUNOGENIC CONJUGATES

[76] Inventor: Porter W. Anderson, 40 Alpine St., Rochester, N.Y. 14620

[21] Appl. No.: 511,048

[22] Filed: Jul. 5, 1983

Related U.S. Application Data

[63] Continuation-in-part of Ser. No. 298,102, Aug. 31, 1981, abandoned.

[51] Int. Cl.[4] .................... A61K 39/02; A61K 39/09; A61K 39/102; C07K 15/04
[52] U.S. Cl. ........................................ 424/92; 530/350
[58] Field of Search ................ 424/88, 92; 260/112 R

[56] References Cited

U.S. PATENT DOCUMENTS

| | | | |
|---|---|---|---|
| 4,196,192 | 4/1980 | Kuo | 424/92 |
| 4,210,641 | 7/1980 | Brossard et al. | 424/180 |
| 4,220,717 | 9/1980 | Kuo | 435/101 |
| 4,411,888 | 10/1983 | Klipstein et al. | 424/92 |
| 4,451,446 | 5/1984 | Vandevelde et al. | 424/92 |
| 4,459,286 | 7/1984 | Hilleman et al. | 424/87 |
| 4,496,538 | 1/1985 | Gordon | 424/92 |

FOREIGN PATENT DOCUMENTS

| | | |
|---|---|---|
| 0060129 | 9/1982 | European Pat. Off. |
| 0098581 | 1/1984 | European Pat. Off. |
| 0109688 | 5/1984 | European Pat. Off. |

OTHER PUBLICATIONS

Uchida, T., et al., Science, vol. 115, pp. 901–903, 1972.
Jennings, H., et al., J. Immunology, vol. 127, pp. 1011–1018, 1981.
Schneerson et al., New Developments with Human and Veterinary Vaccines, Alan R. Liss, Inc. New York, pp. 77–94, (1980).
Stein et al., J. Immunol. 128(3): 1350–1354, (1982).
Galanos et al., European J. Biochem. 8: 332–336, (1969).
Zamenhof et al., J. Biol. Chem. 203: 695–704, (1953).
Beuvery et al., Infect. Immun. 37(1): 15–22, (1982).
Lin et al., Immunol. 46: 333–342, (1982).
Schneersen et al., Progress in Allergy, Karger, Basel, vol. 33, pp. 144–158, (1983).
Anderson, Infect. Immun. 39(1): 233–238, (1983).
Tsay et al., Abstract 3348, Federation Proceedings, vol. 42, No. 4, (Mar. 5, 1983).
Chu et al., Infect. Immun. 40(1): 245–256, (1983).
Ovary et al., Proc. Soc. Exp. Biol. Med. 114, 72–76, (1963).
Geyer et al., Med. Microbiol. Immunol. 165:271, (1979).
Schneerson et al., J. Exptl. Med. 152:361, (1980).
Schwartz and Gray, Arch. Biochem. Biophys, 181:542, (1977).

*Primary Examiner*—Blondel Hazel

[57] ABSTRACT

An immunogenic conjugate which is the reductive amination product of an immunogenic capsular polymer fragment having a reducing end and derived from a bacterial capsular polymer of a bacterial pathogen, and a bacterial toxin or toxoid. The invention also relates to methods for the preparation of the conjugates, a vaccine containing the conjugates which elicits effective levels of anti-capsular polymer antibodies in humans. Also disclosed are methods for inducing active immunization against systemic infection in young mammals caused by bacterial pathogens comprising the administration of an immunogenic amount of the above-described conjugate.

50 Claims, No Drawings

IMMUNOGENIC CONJUGATES

This application is a continuation in part of application Ser. No. 298,102, filed Aug. 31, 1981, now abandoned, which is incorporated herein by references.

TABLE OF CONTENTS

1. Field of the Invention
2. Background of the Invention
   2.1. Conjugation of Intact Capsular Polymers to Protein
   2.2. Vaccines Containing Conjugates
3. Summary of the Invention
4. Detailed Description of the Invention
5. Example: Generation of Large, Medium and Small Fragments of PRP Containing Reducing End Groups
6. Example: Variation of PRP Fragment Ratio to $CRM_{197}$
7. Example: Conjugation of Very Small Fragments of PRP to Diphtheria Toxin, Diphtheria Toxoid and $CRM_{197}$
8. Example: Use of PRP Fragments Conjugated to Diphtheria Toxoid and $CRM_{197}$ as Vaccines in Young Humans
9. Example: Conjugation of Capsular Polymer Fragments of *Streptococcus pneumoniae* to $CRM_{197}$

1. FIELD OF THE INVENTION

This invention relates to the field of novel vaccine compositions, processes for producing them and methods for immunization of young warm-blooded animals, including humans, against infections and disease caused by bacteria, including, for example, *Haemophilus influenzae* type b, *Escherichia coli*, *Neisseria meningitidis* serogroups A and C, *Streptococcus pneumoniae* serotypes 3, 6, 12, 14, 19, 23 and 51, and *Pseudomonas*.

2. BACKGROUND OF THE INVENTION

It is known that purified bacterial capsular polymers (CP) generally are immunogenic in mature humans and animals and can be used as vaccines against the corresponding systemic infections. As used in this application, the term "capsular polymers" refers to sugar-containing polymers, such as polymers of sugars, sugar acids, amino sugars, polyhydric alcohols and sugar phosphates, and does not refer to amino acid-containing polymers. These "capsular polymers" are frequently referred to in the medical literature as "capsular polysaccharides", though they may contain linkages other than glycosidic linkages and constituents other than sugars such as those listed above.

The capsular polymers of different bacteria vary widely in immunogenicity in the first year of human life. Some are moderately active, such as *Streptococcus pneumoniae* serotype 3 and *Neisseria meningitidis* serogroup A. The susceptibility to systemic infection by encapsulated bacteria is greater in the first year of life. The immunogenic response to many bacterial capsular polymers in children is age dependent, i.e., immunocompetence to CP increases to adult levels by about six years of age.

Among the inactive CP are those of *Haemophilus influenzae* type b, *Streptococcus pneumoniae* serotypes 6 and 12, and *Neisseria meningitidis* serogroup C. Examples of CP's which give an intermediate response in infants are *Streptococcus pneumoniae* serotypes 19 and 51.

2.1. INTACT CAPSULAR POLYMERS AS ANTIGENS IN VACCINES

Various investigators have isolated and purified intact capsular polymers which may be useful in or as vaccines. For example, U.S. Pat. No. 4,220,717 describes a process for the isolation and purification of immunologically active polyribosyl ribitol phosphate (PRP) from the capsular polymer of *H. influenzae* b. Additionally, U.S. Pat. No. 4,210,641 relates to polysaccharide extracts of *H. influenzae* having an apparent molecular weight greater than 200,000 daltons and composed principally of galactose, glucose and mannose and containing a small amount of osamines.

Several researchers have utilized these and other intact capsular polymers in formulations to achieve better immunological responses. For example, U.S. Pat. No. 4,196,192 discloses a vaccine containing purified intact PRP and whole *Bordetella pertussis* bacteria. This approach to increasing immunogenicity resulted in enhanced levels of anti-PRP and anti-pertussis antibodies in young mammals.

2.2. VACCINES CONTAINING CONJUGATES

Other researchers have studied conjugation of capsular polymers to carrier proteins in an effort to enhance antibody formation by the so-called "carrier effect". For example, Schneerson et al., Journal of Experimental Medicine 152:361–376 (1980) describes *H. influenzae* b polymer-protein conjugates disclosed to confer immunity to invasive diseases caused by *H. influenzae* b. The reference documents the age-related immunological behavior of capsular polymers in infants and seeks to overcome this age-dependence by conjugation of the intact capsular polymer with a variety of proteins, including serum albumins, *Limulus polyphemus* hemocyanin and diphtheria toxin. The method of conjugation involves the use of a linking agent such as adipic dihydrazide.

Geyer et al., Med. Microbiol. Immunol. 165:171–288 (1979), prepared conjugates of certain *Klebsiella pneumoniae* capsular polysaccharide fragments to a nitrophenyl-ethylamine linker by reductive amination, and the derivatized sugar was then attached to proteins using azo coupling.

3. SUMMARY OF INVENTION

The present invention relates to the covalent attachment of capsular polymer fragments derived from bacterial capsular polymers to bacterial toxins or toxoids by means of reductive amination. As used in the present application, the term "toxoid" means a form of a toxin which has the antigenicity of the toxin without its toxicity.

The immunogenic conjugates of the invention are prepared by first forming reducing end groups on fragments of the capsular polymers and reacting these with amine groups of the bacterial toxin or toxoid by reductive amination. The reducing end groups may be formed by any suitable method, including selective hydrolysis, e.g., by acids or enzymes, or by oxidative cleavage, e.g., by periodate. The conjugation is preferably achieved by reductive amination in an aqueous solution containing cyanoborohydride anions.

The immunogenic conjugates of the invention may be formulated with a pharmaceutically acceptable carrier to produce a vaccine which elicits effective levels of anti-capsular antibody formations in young mammals, including humans. The vaccine may be utilized to induce active immunization against systemic infection in young mammals caused by the respective encapsulated bacteria by administering an immunogenic amount of the conjugate to the mammal.

The immunogenic conjugates have been found to be less age dependent than the capsular polymers alone, and are useful for the active immunization of very young warm-blooded mammals against systemic infections by the respective encapuslated bacteria.

Furthermore, the immunogenic conjugates of the invention do not contain potentially toxic linking agents, such as adipic dihydrazide or p-nitro-phenylethylamine, which have been used in conjugating carbohydrate to protein.

Finally, the immunogenic conjugates of the invention contain fragments of capsular polymers, not intact capsular polymers. The highly repetitive structure of capsular polymers may be in part responsible for their failure to expand the capacity for antibody production in infants. A conjugate of intact (highly polymerized) CP and protein may only partially overcome the immunologic disadvantages of CP alone.

On the other hand, the use of capsular polymer fragments on a carrier may circumvent the disadvantages of the repetitive structure. Additionally, the CP determinants of a conjugate having CP fragments are on the average closer to the carrier than are the CP determinants of conjugates having intact CP, and this proximity to carrier may be necessary for a more effective "carrier effect".

A further advantage lies in the use, for the protein carrier, of a bacterial toxin or toxoid against which children are routinely vaccinated, e.g., tetanus or diphtheria. Desired immunity to the toxin or toxoid is induced along with immunity against the pathogens associated with the capsular polymer.

4. DETAILED DESCRIPTION OF THE INVENTION

The conjugates of the invention are formed by reacting reducing end groups of the capsular polymer fragment to primary amino groups of a bacterial toxin or toxoid to yield antigenic determinants of the capsular polymer covalently linked to the carrier protein. The reducing groups may be formed by selective hydrolysis or specific oxidative cleavage.

Antigenic fragments with at least one reducing end can be generated from capsular polymers by a variety of methods, depending upon the structural features of the particular capsular polymer. Limited oxidative cleavage by periodate (or related reagents) will leave aldehydic termini; such an approach will be limited to polymers having vicinal dihydroxy groups on a non-cyclic residue. Hydrolysis of a glycosidic linkage produces a reducing sugar terminus. Such hydrolysis can be most specifically accomplished enzymatically by glycosidases, but this application would be restricted to a relatively few capsular polymers, e.g., *Streptococcus pneumoniae* 8, for which glycosidases are known. Acidic hydrolysis is commonly used for hydrolysis of glycosidic linkages. The utility of this approach would be limited if the polymer contains acid-sensitive non-glycosidic linkages or if the polymer contains acid-sensitive branch linkages important to the antigenic specificity.

The conjugation is carried out according to the reductive amination process of Schwartz and Gray, Arch. Biochem. Biophys. 181:542–549 (1977). Briefly, the process involves reacting the reducing capsular polymer fragment and bacterial toxin or toxoid in the presence of cyanoborohydride ions, or another reducing agent which will not reduce the reducing ends of interest nor adversely affect the toxin or toxoid capsular polymer. The cyanoborohydrate ions (or their equivalent) act solely as a mild selective reducing agent of the Schiff base intermediate formed between the carbonyl groups of the hydrolyzed capsular polymer fragment and amino groups of the protein. Thus, unlike previously employed conjugation procedures wherein the active molecules are joined by a linking agent which forms a part of the final product, the cyanoborohydride reducing anions utilized herein are not incorporated into the final product. This is important from the standpoint of controlling the potential toxicity of the final product. Evidence of covalent linkage is demonstrated by the fact that the association between, for example, a PRP moiety and the carrier protein persists despite salting-out of the protein in the presence of 8M urea, which has a great ability to disrupt non-covalent bonds.

Suitable carrier proteins are those which are safe for administration to young mammals and immunologically effective as carriers. Safety would include absence of primary toxicity and minimal risk of allergic complications. Diphtheria and tetanus toxoids fulfil these criteria; that is, suitably prepared, they are non-toxic and the incidence of allergic reactions is well documented. Though the risk of allergic reaction may be relatively significant for adults, it is minimal for infants.

In the "carrier effect" a weak antigen, by being attached to a stronger antigen as carrier (i.e., a heterologous protein), becomes more immunogenic than if it were presented alone. If an animal is previously immunized with the carrier alone, it may become "primed" for an enhanced response not only to the carrier antigen but also the attached weaker antigen. Infants are routinely immunized with tetanus and diphtheria toxoids. Thus, they would be primed for subsequent presentation of a capsular polymer antigen conjugated to either of these toxoids.

In general, any heterologous protein could serve as a carrier antigen. However, certain bacterial toxins such as tetanus and diphtheria may have an additional advantage in that they are composed of two portions, one of which (the "binding" subunit) has a strong affinity for binding to mammalian cell surfaces. Conceivably, conjugation to such a "binding" protein would permit the carried antigen to more effectively initiate responses in cells of the immune system.

The carrier proteins to which the capsular polymer is conjugated may be native toxin or detoxified toxin (toxoid). Also, by relatively recent mutational techniques, one may produce genetically altered proteins which are antigenically similar to the toxin yet non-toxic. These are called "cross reacting materials", or CRMs. $CRM_{197}$ is noteworthy since it has a single amino acid change from the native diphtheria toxin and is immunologically indistinguishable from it.

A culture of *Corynebacterium diphtheriae* strain C7 ( 197), which produces $CRM_{197}$ protein, has been deposited with the American Type Culture Collection, Rockville, Maryland and has been assigned accession number ATCC 53281.

Conjugation of capsular polymer to native toxin may reduce toxicity, but significant toxicity may remain. Thus, further detoxification would be required. Conventional detoxification of protein toxins employs formalin, which reacts with free amino groups of the protein. Residual toxicity may still be a concern. Furthermore, spontaneous retoxification is possible with any particular lot of vaccine and remains an issue of concern with this approach.

Alternatively, native toxin may be detoxified with formalin to produce conventional toxoid before conjugation to capsular polymer. However, the prior formalin treatment reduces the number of free amino groups available for reaction with the reducing groups of the capsular polymer fragment. CRMs, thus, have significant advantages in that they have no inherent toxicity yet none of their amino groups are occupied by the formalin. A further advantage is that no biohazards exist in working with CRMs.

In the case of $CRM_{197}$, which is immunologically identical to native toxin, treatment with formalin (though there is no need to detoxify) greatly enhances the immunological response. It is thought that this is due to stabilization of the molecule against degradation by mechanisms of the body and/or aggregation by cross-linking (immunogenicity of particles increases with size).

For all of the above reasons, tetanus and diphtheria toxins are prime candidates for carrier proteins, yet there are others which may also be suitable. Though these others may not have the history of safety found with diphtheria and tetanus, there may be other overwhelming reasons to use them. For instance, they may be even more effective as carriers, or production economics may be significant. Other candidates for carriers include toxins of pseudomonas, staphylococcus, streptococcus, pertussis and *Escherichia coli*.

Suitable carrier media for formulating a vaccine include sodium phosphate-buffered saline (pH 7.4) or 0.125M aluminum phosphate gel suspended in sodium phosphate-buffered saline at pH 6 and other conventional media.

Generally, vaccines containing from about 5 to about 100 μg, preferably about 10 to 50 μg, are suitable to elicit effective levels of antibody against the capsular polymer in young warm-blooded mammals. Of course, the exact dosage would be determined by routine dose/response experimentation. Several small doses given sequentially would be expected to be superior to the same amount of conjugate given as a single injection.

The vaccines of the invention may be administered by injection to warm-blooded mammals of any age and is especially adapted to induce active immunization against systemic infections in young mammals caused by the pathogens *Haemophilus influenzae* type b, *Escherichia coli*, pneumococcus, meningococcus, streptococcus and pseudomonas.

The following are non-limiting examples of methods for the preparation of exemplary immunogenic conjugates of the present invention and their use in vaccines.

5. EXAMPLE: GENERATION OF LARGE, MEDIUM AND SMALL FRAGMENTS OF PRP CONTAINING REDUCING END GROUPS AND CONJUGATION TO $CRM_{197}$

The capsular polymer of *Hemophilus influenzae* type b is a linear polymer with the repeating unit [-3-β-D-ribosyl(1-1)ribitol(5-phosphate)-] (PRP). Generally, hydrolysis of PRP is carried out until the ratio of total to reducing ribose has dropped to 25 or below. The resulting mixture of size fragments may be fractionated by molecular sieve column chromatography to isolate the desired size range of fragments for conjugations. The method for obtaining fragments is as follows:

a. A sample of sodium PRP, (nucleic acid content 0.006%) containing 28.6 milligrams ribose was dissolved with distilled water to make a total volume of 9.2 ml in a 125-ml erlenmeyer flask and chilled in ice.
b. 1.02 ml of $0.1N_2SO_4$ was added.
c. Duplicate samples of 0.01 ml of the acidified PRP were transferred to test tubes held on ice (0-minute)
d. The flask was transferred to a boiling-water bath for 3 minutes, then chilled in an ice-water bath.
e. Step c was repeated (3-minute sample).
f. The samples were assayed for reducing power by the alkaline ferricyanide method standarized with D-ribose.
g. Based on the result (see Table 1), step d was repeated.
h. Step c was repeated (6-minute samples).
i. Step f was repeated.

TABLE 1

| Samples | Nanomoles of reducing ribose (av) | Ratio, total ribose/ reducing ribose |
|---|---|---|
| 0-min | 0.42 | 493 |
| 3-min | 6.08 | 34.0 |
| 6-min | 9.66 | 21.4 |

The result (see Table 1) indicated that, assuming the sole mode of hydrolysis had been at the (1-1) glycosidic linkage, the number-average chain length was 21.4 monomeric units, i.e., (ribitol-5-phosphate-3-ribose)

j. 0.102 ml 1N NaOH was added, and the pH was estimated by indicator paper (about pH 6).
k. The neutralized hydrolysate was lyophilized.
l. Bio-Gel P10 (Bio-Rad, Inc.) was equilibrated in 0.1M triethylammonium acetate and poured into a 1.5 cm diameter chromatographic column, giving a gel-bed height of 98 cm.
m. The lyophilized material (step k) was rehydrated with 2.7 ml water, and 0.3 ml of 1M triethylammonium acetate was added. This solution was applied to the column and elution was carried out with collection of 3.5 ml fractions.
n. The elution of ribosyl residues was determined by assay of 0.005-ml samples of each fraction for ribose content by the orcinol reaction with D-ribose as standard.
o. Fractions were combined into 3 pools, L, M, and S as indicated in Table 2, and the pools were assayed for total ribose and reducing ribose:

TABLE 2

| Pool | Fractions contained | Total ribose, micromoles | Ratio, total ribose/ reducing ribose | Est. Mn* | Range of Ve/Vo of fraction |
|---|---|---|---|---|---|
| L | 15–18 | 577 | 31.2 | 11,000 | ≦1.08 |
| M | 19–23 | 744 | 18.6 | 6800 | 1.09–1.38 |
| S | 24–34 | 1180 | 9.1 | 3400 | 1.39–1.99 |

*on the assumption that the sole hydrolsis was glycosidic.

p. The pools were lyophilized, re-hydrated with 10 ml water, re-lyophilized, re-hydrated with 1.5 ml water. 1.2 ml of the last solutions were transferred to microcentrifuge tubes and lyophilized in preparation for the conjugation reactions.

Conjugation of $CRM_{197}$ to Reducing Fragments of PRP a. To the microcentrifuge tubes containing lyophilized fragments, L, M, and S and an empty tube (C or control) were added potassium phosphate buffer pH 8, 2.7 milligrams $CRM_{197}$, and 4 milligrams sodium cyanoborohydride, such that the final volume was 0.2 ml and the phosphate buffer was at 0.2M.

b. The tubes were incubated at 37° C. with daily mixing.

c. After 18 days the tubes were centrifuged 2 minutes at 7000 G.

d. After determination that the majority of protein was in the precipitates, the precipitates were washed four times with ≦1 ml water.

e. The washed precipitates were made 8M in urea and warmed to 50° C., dialyzed against saline overnight at 4° C., and centrifuged. The supernates were separated and made 95% saturated in ammonium sulfate, held overnight at 4°, and centrifuged. The resulting precipitates were washed 3 times with 0.4 ml of 95% saturated ammonium sulfate, and suspended with 1 ml water. These colloidal suspensions were labeled $CRM_{197}$-PRP-L, -M, -S, and $CRM_{197}$-C, respectively.

f. The preparations were assayed for protein by means of the Folin phenol reaction with bovine albumin as standard and for ribosyl residues with the orcinol reaction and D-ribose as standard. The results are given in Table 4. The preparations were assayed for PRP antigenic activity by their ability (at concentrations of 50 micrograms protein/ml) to inhibit the binding of labeled native PRP to human anti-PRP antibody (Table 3).

TABLE 3

| Preparation tested | % Antigen bound | antigenic activity, ng PRP equivalence/μg protein |
|---|---|---|
| none | 28.1 | — |
| > native PRP, 0.5 ng/ml | 6.7 | — |
| > native PRP, 5 ng/ml | 0.94 | — |
| $CRM_{197}$ - C | 34.3 | 0.0 |
| $CRM_{197}$ - PRP-S | 2.0 | 0.1 |
| $CRM_{197}$ - PRP-M | 2.5 | 0.08 |
| $CRM_{197}$ - PRP-L | 3.9 | 0.006 |

Thus, all the tested conjugates of $CRM_{197}$ with PRP fragments were antigenically active, while the control preparation in which $CRM_{197}$ was exposed to cyanoborohydride in the absence of PRP fragments was inactive as expected.

The preparations were assayed for immunogenicity in rabbits in comparison with high molecular weight purified PRP, and the results are given in Table 4. Rabbits given the PRP control or the $CRM_{197}$ -C control made barely detectable increases in anti-PRP antibody. Rabbits given any of the three $CRM_{197}$ -PRP conjugates made progressive increases after each injection; the titers after the third injection were 1000-fold greater than prior to immunization. In an experiment not illustrated a simple mixture of $CRM_{197}$ and PRP fragment preparation L was assayed in rabbits and found not to elicit anti-PRP antibody.

TABLE 4

ANTI-PRP ANTIBODY RESPONSE TO CONJUGATED AND CONTROL VACCINES OF WEANLING RABBITS PRIMED WITH ORDINARY DIPHTHERIA TOXOID*

| Rabbit | Vaccine** | Pentose/protein ratio | Anti-PRP Antibody, ng/ml, at age in weeks 7*** | 8*** | 9*** | 10 |
|---|---|---|---|---|---|---|
| 1 | PRP(MW $10^5$) | | <10 | 12 | 28 | 40 |
| 2 | " | | <10 | <10 | 27 | 26 |
| 3 | $CRM_{197}$-C (control) | — | 35 | 25 | 31 | 36 |
| 4 | " | | 16 | 34 | 40 | 48 |
| 5 | $CRM_{197}$-PRP-S | 0.015 | 19 | 980 | 26,000 | 49,000 |
| 6 | " | | <10 | 84 | 23,000 | 31,000 |
| 7 | $CRM_{197}$-PRP-M | 0.0069 | <10 | 37 | 2,500 | 11,000 |
| 8 | " | | 23 | 11,000 | 49,000 | 150,000 |
| 9 | $CRM_{197}$-PRP-L | 0.0020 | 14 | 73 | 3,700 | 26,000 |
| 10 | " | | <10 | 340 | 9,800 | 76,000 |

*The rabbits were New Zealand Whites obtained from Dutchland Farms immediately after weaning. At six weeks of age each was injected subcutaneously (s.c.) with 40 Lf of diphtheria toxoid (Massachusetts Dept. of Public Health) contained in 0.5 ml of 0.0125 M aluminum phosphate pH 6 (alum).

**The PRP vaccine was 30 μg PRP lot 17 contained in 0.1 ml saline. The other vaccines were 25 μg protein contained in 0.5 ml alumn.

***Injections of the indicated vaccine were given (s.c.) immediately after bleeding. There were two rabbits per vaccine. Listed are individual titers, determined by radio-antigen binding with $^3$H-labeled native PRP.

The protective potential of the anti-PRP antibodies induced by the conjugates was evaluated by testing the bactericidal activity of the rabbit sera of Table 4. The bactericidal titers were determined against *H. influenzae* b strain Eag by the methods of Anderson et al, Journal of Clinical Investigation, Volume 65, pages 885-891 (1980). Table 5 shows that before vaccination the sera were unable to kill the bacteria (reciprocal titers <2). After three injections the reciprocal titers of the rabbits receiving the $CRM_{197}$- PRP conjugates had risen to 16 or greater while titers of the rabbits receiving the CRM 197 control remained at <2.

TABLE 5

Bacterial Titers Against *H. influenzae* b Strain Eag of Sera of Weanling Rabbits Vaccinated With $CRM_{197}$ of Its Conjugates With Oligosaccharides S, M, and L of PRP*

| Rabbit | Vaccine given | Reciprocal serum dilution for > 90% Killing: Pre-vaccination | After 3 injections |
|---|---|---|---|
| 3 | $CRM_{197}$ control | <2 | <2 |
| 4 | $CRM_{197}$ control | <2 | <2 |
| 5 | $CRM_{197}$-PRP-S | <2 | 128 |
| 6 | $CRM_{197}$-PRP-S | <2 | ≧256 |
| 7 | $CRM_{197}$-PRP-M | <2 | 16 |
| 8 | $CRM_{197}$-PRP-M | <2 | 64 |
| 9 | $CRM_{197}$-PRP-L | <2 | 64 |
| 10 | $CRM_{197}$-PRP-L | <2 | 32 |

*Same vaccinations as described in Table 4.

6. EXAMPLE: VARIATION OF PRP FRAGMENT RATIO TO $CRM_{197}$

In this example, the ratio of PRP fragment S to $CRM_{197}$ was varied and the conservation of antigenic activity of the $CRM_{197}$ component was examined in addition to the PRP component.

Preparation of $CRM_{197}$-PRP-S#2, A and B.

a. To microcentrifuge tubes A and B were added 0.15 ml each of the solution of fragments S described above, i.e., steps o and p. The solutions were lyophilized.

b. Tube A received 0.015 ml 2M potassium phosphate buffer pH 8, 0.1 ml of $CBM_{197}$ 5 mg/ml in 0.01M sodium phosphate buffer pH 7, and 0.015 ml of sodium cyanoborohydride 200 mg/ml.

c. Tube B received 0.002 ml of the pH 8 buffer and 0.1 ml of the $CRM_{197}$ solution. The resulting solution was lyophilized. The solids were suspended with 0.015 ml water, and 0.002 ml of the pH 8 buffer were added.

d. Tubes A and B were incubated at 37° C. for 13 days. To tube B an additional 0.002 ml of cyanoborohydride was added. Both tubes were incubated at 37° C. for an additional 3 days. (Note that due to the reduced reaction volume, the concentrations of reactants in B were higher than A.)

e. To A was added 0.06 ml water and 0.8 ml saturated ammonium sulfate (SAS). To B was added 0.175 ml water and 0.8 ml SAS.

f. The tubes were incubated 1 hour at 0° C. and centrifuged 20 minutes at 8000 G. The supernates were removed.

g. The precipitates were washed by suspension in 1 ml of 80% SAS, centrifugation at 8000 G 20 minutes, and removal of the supernates.

h. The precipitates were suspended with 0.1 ml water, and 0.4 ml SAS was added.

i. Same as step f.

j. Same as step g.

k. The precipitate in B was dissolved with 0.084 ml 9.5M urea (estimated final concentration 8M); 0.1 ml water and 0.8 ml SAS were added, and the precipitate was isolated as in step f. This precipitate was washed as in step g.

l. The precipitates in A and B were suspended with 0.2 ml water. The suspensions were separated into soluble (s) and insoluble (i) fractions by centrifugation 30 minutes at 8000 G, and the s fractions (supernates) were made 0.01M sodium phosphate buffer pH and reserved.

m. The i fractions (precipitates) were rendered more soluble as follows: they were made 8M in urea, which was then gradually removed by dialysis against 0.01M sodium phosphate buffer pH 7. The resulting solutions were recombined with the respective s fractions.

n. Preparations A and B were tested for protein content with the Folin phenol reagent and for PRP antigenic activity by the assay described above. Both had PRP activity; B exceeded A by about 13-fold, as shown below:

| Preparation | ng PRP equivalence/μg protein |
|---|---|
| $CRM_{197}$-PRP-S#2,A | 0.038 |
| $CRM_{197}$-PRP-S#2,B | 0.50 | o. Preparations A and B were tested for CRM antigenicity (activity as diphtheria toxoid (DT)) by inhibition of the binding of antibody to a sample of purified DT furnished by the Massachusetts Department of Public Health. Both had activity roughly equal to the DT on a weight basis; B exceeded A by about 4-fold, as shown below.

| Inhibitor tested | Antibody bound, $A_{400}$ | μg DT equivalence per μg protein |
|---|---|---|
| None | 2.43 | |
| DT, 0.5 μg/ml | 2.56 | |
| DT, 5 μg/ml | 1.93 | |
| DT, 50 μg/ml | 0.96 | |
| $CRM_{197}$-PRP-S#2,A,50 μg/ml | 1.25 | 0.52 |
| $CRM_{197}$-PRP-S#2,B 5 μg/ml | 1.67 | 2.0 | p. Preparations A and B were suspended in alum at 16 ug protein 1 ml, and three 0.5 ml injections were given to rabbits in the protocol described in Table 4 (except the animals were 8 weeks old at the onset and not primed by previous injections of diphtheria toxoid). The sera were tested for antibodies in the binding assay described in step o. Both A and B elicited antibodies to DT as well as to PRP, as shown in Table 6. Separate control experiments showed that similar rabbits housed in the same quarters did not display such increases in anti-DT antibody values in the absence of being injected with $CRM_{197}$ preparations.

TABLE 6

| Rabbit | Injected | Assay for antibody to | Antibody values at age | | | |
|---|---|---|---|---|---|---|
| | | | 8 wk | 9 wk | 10 wk | 11 wk |
| 5 | A | PRP, ng/ml | 47 | 60 | 210 | 13,500 |
| | | DT, $A_{400}$ | 0.136 | 0.168 | 1.28 | 3.81 |
| 6 | A | PRP | 21 | 25 | 19 | 420 |
| | | DT | 0.072 | 0.049 | 0.262 | 3.23 |
| 7 | A | PRP | <20 | 20 | 2000 | 10,500 |
| | | DT | 0.155 | 0.134 | 0.155 | 0.676 |
| 3 | B | PRP | <20 | 27 | 1600 | 4900 |
| | | DT | 0.075 | 0.061 | 0.227 | 2.45 |
| 8 | B | PRP | 23 | <20 | 2900 | 26,000 |
| | | DT | 0.065 | 0.023 | 0.231 | 2.07 |

7. EXAMPLE: CONJUGATION OF VERY SMALL FRAGMENTS OF PRP TO DIPHTHERIA TOXIN, DIPHTHERIA TOXOID AND $CRM_{197}$

Generation of Very Small Fragments of PRP Containing Reducing End Groups a. A 12 ml solution of PRP lot 20 was made 0.1M in HCl at 0° C. and sealed in a glass flask (0 minute).

b. The flask was transferred to a boiling-water bath for 4 minutes, then chilled in an ice water bath.

c. A small amount of resulting white colloid was removed by extraction with ether and the resulting clear solution was lyophilized.

d. Bio-Gel P10 (Bio Rad, Inc.) was equilibrated in 0.01M ammonium acetate and poured into a 1.5 cm diameter chromatographic column, giving a gel bed height of 98 cm.

e. The lyophilized material was rehydrated with 1.5 ml water and neutralyzed with $NH_4OH$. This solution was applied to the column and the elution was carried out.

f. Fragments eluting at Ve/Vo range of 2.0–2.4 were collected and designated fraction vs.

g. Steps a–f were repeated to double the supply of fraction vs.

h. The combined vs fractions were lyophilized, rehydrated to yield 4 ml of a solution containing a total of 47 umoles of reducing sugar activity when assayed by the alkaline ferricyanide method standardized with D-ribose.

Preparation of Conjugates of PRP-vs Fragments to Native Diphtheria Toxin, Native Diphtheria Toxoid and $CRM_{197}$ The following proteins are used as carriers in the present example:
(1) DTx—purified diphtheria toxin, lot 1, obtained from the Massachusettes Public Health Biologic Laboratories. Partial detoxification is accomplished by the linking to PRPvs. Residual toxicity is removed by formalin treatment in the presence of lysine by the method of Pappenheimer et al., Immunochemistry, 9:891 (1972).

(2) DTd—conventional (formal) toxoid, lot DCP-27, also obtained from the Massachusettes laboratories.

(3) $CRM_{197}$—antigenically mutated version of the toxin protein, antigenically indistinguishable from toxin but non-toxic.

The conjugation method is as follows:

a. Protein, potassium phosphate buffer (pH 8.0 at 25° C.) and PRPvs were combined in glass centrifuge tubes in the manner set out below.

| Solution | Protein | Buffer | PRPvs |
|---|---|---|---|
| (1) | 30 mg DTx | 0.24 μmol | 20 μmol |
| (2) | 30 mg DTd | 0.24 μmol | 20 μmol |
| (3) | 10 mg $CRM_{197}$ | 0.08 μmol | 6.7 μmol | b. The solutions were lyophilized, and the lyophiles were dissolved with $NaCNBH_3$ solution, 2% w/v in water as tabulated below.

| Solution | 2% $NaCNBH_3$ |
|---|---|
| (1) | 1.2 ml |
| (2) | 1.2 ml |
| (3) | 0.4 ml | c. The tubes were incubated at 37° C.

d. After 14 days, four volume-equivalents of saturated ammnonium sulfate were added. These suspensions were held 3 hours at 0° C., then centrifuged 20 minutes at 9000 G.

e. The precipitates were washed twice each with 10 ml of neutral 70% saturated ammonium sulfate.

f. The washed precipitates were dissolved with a minimal volume of 9.5M urea and dialyzed against 0.067M sodium phosphate buffer, pH 7.8.

Formalin Treatment of the Conjugates a. The conjugates were further dialyzed against sodium phosphate buffer which also contained 0.025M lysine. (Small samples were reserved for toxicity testing prior to formalinization).

b. Formalin was added to a final concentration of 0.2% v/v.

c. After 17 days incubation at about 24° C. the solutions were extensively dialyzed against the sodium phosphate buffer.

d. Centrifugation was performed to remove small amounts of insoluble material.

Processing to Achieve Final Container Products a. Antigen solutions (1)-(3) in isotonic sodium phosphate buffer were passed through 0.22-micron "Millex" filter units (Millipore Corp.) and injected into bottles containing sterile phosphate buffered saline.

b. The preparations were assayed for protein using the Lowry method.

c. Thimerosal was filtered and injected into the solution as 1/100 volume of a freshly made 1% w/v solution. Samples of 10 ml were taken for a sterility test. The bottles were attached to a manually operated sterile single use filling device (Multiple Additive Set, Travenol Laboratories). 2-ml glass vials were filled, stoppered, sealed, and immediately transferred to storage at 4° C.

Assays on Conjugate Preparations a. Phosphate content of the protein fraction

PRP is composed of the repeating unit ribosyl-ribitol-phosphate. Thus colorimetric assay of phosphate in the fraction precipitable by 5% tricholoracetic acid (TCA) is a sensitive index of the incorporation of PRP fragments into the protein.

Samples containing 100 μg protein were made 5% in TCA in a volume of 3 ml, held 20 minutes on ice, and centrifuged 15 minutes at 4° C. at G. The precipitates were washed with an additional 3 ml of 5% TCA, then with 5 ml ethanol. The washed precipitates were ashed to convert organic phosphate to inorganic phosphate (Pi), and the Pi was quantified by the method of Chen et al., Anal. Chem., 28:1756 (1956). The results were as follows:

| Sample | nmol Pi/ μg protein | Implied average no. of PRP repeating units/protein |
|---|---|---|
| (1) DTx-PRPvs | 0.11 | 6.8 |
| (2) DTd-PRPvs | 0.10 | 6.2 |
| (3) $CRM_{197}$-PRPvs | 0.10 | 6.2 | b. Electrophoretic Analysis

Samples of the conjugated antigens were analyzed by mercaptoethanol-sodium dodecyl sulphate-polyacrylamide gel electrophoresis (ME-SDS-PAGE) in the same gel alongside the respective starting carrier protein preparations.

DTd-PRPvs, like the DTd, displayed a disperse band at MW 61,000 daltons. In contrast, DTx-PRPvs and $CRM_{197}$-PRPvs differed greatly from the starting proteins. The protein of these two conjugates collected either at the beginning of or in the stacking gel (4% acrylamide) or at the beginning of the separating get (10% acrylamide). Thus, the conjugates appear to have been converted into macromolecular aggregates, presumably by cross-linking from the formalin treatment. DTd-PRPvs also contains some aggregated material.

c. PRP Antigen Equivalence per Unit Protein

The capacity of the conjugates to bind anti-PRP antibody was determined by the inhibition of the binding of labeled PRP by human anti-PRP antiserum, calibrated with PRP lot 19. (Because protein-bound polymer fragments cannot be assumed to bind to antibody in a weight-equivalent fashion to the high molecular weight polymer, quantitative chemical composition cannot be inferred from these data.)

| Sample | % Inhibition of $^3H$-PRP bound | ng PRP equivalence/ μg protein |
|---|---|---|
| PBS control | (0) | — |

-continued

| Sample | % Inhibition of ³H-PRP bound | ng PRP equivalence/ μg protein |
|---|---|---|
| PRP 19, 0.5 ng/ml | 6.7 | — |
| PRP 19, 5 ng/ml | 32 | — |
| PRP 19, 50 ng/ml | 90 | — |
| DTx-PRPvs, 5 μg protein/ml | 24 | 0.5 |
| DTd-PRPvs, 5 μg protein/ml | 48 | 2.2 |
| CRM₁₉₇-PRPvs, 5 μg protein/ml | 38 | 1.4 | d. Diphtheria Toxoid Antigenic Equivalene Per Unit Protein

Retention of the capacity of the preparations to react with anti-DTd antibody was determined by inhibition of an enzyme-linked immunosorbent assay (ELISA) in which purified DTd is attached to the assay tube (solid phase). Inhibition of antibody binding to the attached DTd is calibrated by the same DTd used in the fluid phase.

| Sample | % Inhibition of Antibody Binding | μg DTd equivalence/ ug protein |
|---|---|---|
| PBS control | (0) | — |
| DTd, 5 μg protein/ml | 24 | — |
| DTd, 50 μg protein/ml | 50 | — |
| DTx-PRPvs, 50 μg protein/ml | 46 | 0.68 |
| DTd-PRPvs, 50 μg protein/ml | 58 | 2.1 |
| CRM₁₉₇-PRPvs, 50 μg protein/ml | 26 | 0.11 | e. Diphtheria Toxic Activity

Samples of the original DTx and the conjugate DTx-PRPvs before and after formalin treatment were titrated for toxic activity by injection into the skin of a non-immune adult rabbit. DTx at doses of 0.002 $\mu$g and 0.02 $\mu$g produced the expected dermal lesions. DTx-PRPvs prior to formalin treatment produced dose-dependent lesions such that 0.2 $\mu$g was approximately equal to 0.002 $\mu$g DTx (100-fold reduction in toxicity by the conjugation). After formalin treatment, lesions were not generated by doses as high as 2 $\mu$g (at least 1000-fold reduction relative to DTx). Doses up to 2 $\mu$g of conjugates DTd-PRPvs and CRM₁₉₇-PRPvs were tested similarly and generated no lesions.

f. Induction of Anti-PRP Antibody Responses in Weanling Rabbits, Measured by Radioantigen binding The antigens were mixed with an aluminum phosphate adjuvant (0.0125M Al, pH 6) such that a 0.5 ml dose contained 25 $\mu$g protein. Two rabbits (for each antigen) were given three weekly injections beginning at age 7 weeks; the rabbits had been injected with DTd alone at age 5 weeks, for a hypothetical "carrier priming" effect. All the animals (rabbits 1-6) had anti-PRP rises in an anamnestic pattern, with titers of at least 10 $\mu$g/ml after the third vaccination. Antigens CRM₁₉₇-PRPvs and DTd-PRPvs were also tested in pairs of rabbits that had not been "primed" with DTd. These (rabbits 7-10) produced strong anti-PRP reponses similar to those in the "primed" rabbits.

g. Induction of Anti-DTd Antibody Response in Weanling Rabbits, Measured by ELISA The anti-DTd antibody responses in the same "unprimed" rabbits (7-10) of the preceding subsection are as follows: Rises were roughly 10-fold after the second injection and another 2-to 5-fold after the third.

h. Sterility of the Sample Preparations

The samples were found to be sterile as determined using Fluid Thioglycollate (BBL cat. no. 11260, lot D4D LKL) as the growth medium.

8. EXAMPLE: USE OF PRP FRAGMENTS CONJUGATED TO DIPHTHERIA TOXOID AND CRM₁₉₇ AS VACCINES IN YOUNG HUMANS

Two groups of 8 children in the age range of 1 to 2 years old, (and specifically exempting children receiving routine vaccination with diphtheria toxoid protein at age 18 months) were given primary and secondary vaccinations as follows: Group I received injections of CRM₁₉₇-PRPvs, preparation as described in the preceding section, (25 $\mu$g protein in saline, subcutaneously); Group II received injections of DTd - PRPvs, preparation as described in the preceding section, (25 $\mu$g protein in saline, subcutaneously).

In the first visit, pre-vaccination blood specimens were taken; the child was vaccinated, then observed for 20 minutes for any sign of an anaphylactic reaction. In the second visit the procedure of the first visit was repeated. In the third visit, a post-secondary blood specimen was taken. Two of the children, one from each group, after consultation with the parents, were given a third vaccination to try to raise the antibody against PRP to protective levels. The interval between vaccinations was $1\pm\frac{1}{2}$ month.

Group III consisted of children about 18 months old receiving a vaccine simultaneously with diphtheria toxoid protein in a separate site. This group contained 2 children; one received the CRM₁₉₇-PRPvs vaccine, the other received the DTd-PRPvs vaccine.

Symptoms were recorded for four successive days, with measurements of temperature, notation of behavioral indications of systemic illness and observations of inflammation at the injection site. These symptoms are summarized in Table 7.

TABLE 7

ADVERSE REACTIONS TO PRP-VS CONJUGATES TO CRM₁₉₇ AND FORMAL DIPHTHERIA TOXOID

| Vaccine | Symptom | Injection Primary | Secondary | Tertiary |
|---|---|---|---|---|
| CRM₁₉₇-PRPvs | Fever | 1/8 | 0/8 | 0/1 |
| | Unusual behavior | 0/8 | 0/8 | 0/1 |
| | Local inflammation | 1/9* | 2/9 | 0/1 |
| | Local pain | 1/9* | 1/9 | 0/1 |
| DTd-PRPvs | Fever | 0/8 | 0/8 | 0/1 |
| | Unusual behavior | 0/8 | 0/8 | 0/1 |
| | Local inflammation | 1/9* | 0/9 | 0/1 |
| | Local pain | 1/9 | 1/9 | 0/1 |

*Includes one child who received diphtheria toxoid protein simultaneously in a separate site. No local symptoms were found. Systemic symptoms are not noted since these could not be distinguished from an effect of the diphtheria toxoid protein vaccine.

After CRM₁₉₇-PRPvs vaccination, one child had mild fever (99.8° C.) on the evening of primary vaccination; there was an instance of mild local inflammation once each after a primary, a secondary, and the one tertiary vaccination. After DTd-PRPvs there was an instance of local inflammation after one primary and one secondary vaccination. The administration of the vaccines was otherwise apparently free of adverse reactions.

Serum Antibody Responses

Antibodies to PRP as well as IgG antibodies to diphtheria toxoid were determined. After vaccination with CRM$_{197}$PRPvs a consistent anti-PRP response pattern was seen. See Table 8. There was a distinct rise after the primary injection, usually an even larger rise after the secondary injection, and a large rise after the one tertiary. The final titers greatly exceeded those that have been produced by vaccination with PRP alone and greatly exceeded the accepted estimated protective minimal level of 0.15 μg/ml. The enhanced response was particularly evident in the four children under 18 months of age, where the response to PRP alone is generally inadequate for protection, and the geometric mean of the final titers in these four (8.4 μg/ml) is 175 times that found after vaccination of children 12–17 months old with PRP vaccine alone. The child receiving the primary vaccination simultaneously with diphtheria toxoid protein vaccine also had an excellent response.

IgG antibodies to diphtheria toxoid increased in 6 of 8 children (as well as in the 9th, who also received diphtheria toxoid as part of the treatment). The antibody levels often increased so greatly that the dilution of post-vaccination serum used (1/1000) was insufficient to show the full extent of the rise.

After vaccination with DTd-PRPvs anti-PRP responses generally increased after both primary and secondary vaccination. (See Table 9). However, there were two children (12 and 14 month old) in whom no response was detected; and one child did not approach the protective level until given a third injection. The child receiving the primary vaccination simultaneously with diphtheria toxoid protein had an excellent response. Rises in IgG antibody to the diphtheria component were found in all children.

TABLE 8

| ANTIBODY RESPONSE TO CRM$_{197}$-PRPvs | | | | |
|---|---|---|---|---|
| | Age at primary | Serum | Serum antibody, μg/ml | |
| Subject | vaccination | sample | anti-PRP | IgG anti-DTd |
| 1 | 12 mo | pre-vac | 2.0 | 1.1 |
| | | post-1 | 4.5 | >10 |
| | | post-2 | 18 | >10 |
| 2 | 13 mo | pre-vac | <0.006 | 0.38 |
| | | post-1 | 0.040 | 1.7 |
| | | post-2 | 0.35 | 2.2 |
| | | post-3 | 4.8 | 1.9 |
| 3 | 14 mo | pre-vac | <0.020 | 4.5 |
| | | post-1 | 0.12 | 3.3 |
| | | post-2 | 2.0 | 4.3 |
| 4 | 16 mo | pre-vac | 0.025 | 0.06 |
| | | post-1 | 0.92 | 5.7 |
| | | post-2 | 29 | 9.1 |
| 5 | 27 mo | pre-vac | 0.025 | 3.0 |
| | | post-1 | 10 | >10 |
| | | post-2 | 58 | >10 |
| 6 | 29 mo | pre-vac | 0.13 | 6.1 |
| | | post-1 | 22 | 6.9 |
| | | post-2 | 180 | 7.4 |
| 7 | 30 mo | pre-vac | 2.2 | 6.5 |
| | | post-1 | 28 | >10 |
| | | post-2 | 50 | >10 |
| 8 | 30 mo | pre-vac | 1.3 | 4.8 |
| | | post-1 | 6.5 | >10 |
| | | post-2 | 78 | >10 |
| 9 | 18 mo* | pre-vac | 0.34 | 3.1 |
| | | post-1 | 1.4 | >10 |
| | | post-2 | 8.2 | >10 |

*First injection of CRM$_{197}$-PRPvs given simultaneously with diphtheria toxoid protein vaccine in a separate site

TABLE 9

| ANTIBODY RESPONSE TO DTd-PRPvs | | | | |
|---|---|---|---|---|
| | Age at primary | Serum | Serum antibody, μg/ml | |
| Subject | vaccination | sample | anti-PRP | IgG anti-DTd |
| 1 | 12 mo | pre-vac | <0.020 | 0.060 |
| | | post-1 | <0.020 | 10 |
| | | post-2 | <0.020 | 10 |
| 2 | 12 mo | pre-vac | 0.055 | 0.03 |
| | | post-1 | 0.080 | 3.1 |
| | | post-2 | 1.8 | 10 |
| 3 | 13 mo | pre-vac | <0.006 | 1.1 |
| | | post-1 | <0.006 | 10 |
| | | post-2 | 0.023 | 10 |
| | | post-3 | 0.120 | 10 |
| 4 | 14 mo | pre-vac | <0.020 | 3.0 |
| | | post-1 | <0.020 | 5.1 |
| | | post-2 | <0.020 | 3.8 |
| 5 | 19 mo | pre-vac | 0.060 | 8.0 |
| | | post-1 | 0.12 | 10 |
| | | post-2 | 0.76 | 10 |
| 6 | 26 mo | pre-vac | <0.020 | 6.9 |
| | | post-1 | 0.060 | 10 |
| | | post-2 | 0.94 | 10 |
| 7 | 27 mo | pre-vac | 1.4 | 6.1 |
| | | post-1 | 7.4 | 10 |
| | | post-2 | 21 | 10 |
| 8 | 28 mo | pre-vac | <0.020 | 8.7 |
| | | post-1 | 0.63 | 10 |
| | | post-2 | 8.0 | 10 |
| 9 | 18 mo* | pre-vac | 1.9 | 0.11 |
| | | post-1 | 2.9 | 10 |
| | | post-2 | 11 | 10 |

*First injection of DTd-PRPvs given simultaneously with diphtheria toxoid protein vaccine in a separate site This example shows that injections of conjugates of the H. influenzae b capsular polymer fragment to diphtheria toxoid and CRM$_{197}$ is apparently harmless. CRM$_{197}$-PRPvs vaccination gave a clear indication of an enhancement of the anti-PRP response by the carrier effect —appreciated not only by the high titers but by the rises after secondary vaccination.

DTd-PRPvs had a less impressive enhancement. A likely explanation is that while CRM$_{197}$-PRPvs is a multimolecular aggregate, DTd-PRPvs is present mainly in unimolecular form similar to the original toxoid.

9. EXAMPLE: CONJUGATION OF CAPSULAR POLYMER FRAGMENTS OF STREPTOCOCCUS PNEUMONIAE TO CRM$_{197}$

Several other bacteria resemble H. influenzae b in that they cause sepsis and meningitis, particularly in infants; they have polymer capsules, antibodies to which are protective; and their capsular polymers are immunogenic in mature humans but not in infants. An important example is Streptococcus pneumoniae (Sp) serotype 6. It causes not only the life-threatening infections mentioned above but also is a highly prevalent cause of otitis media in children. (Gray et al, Journal of Infectious Diseases, Volume 142, pages 923–33, 1980).

The approach described for PRP is also applicable to any capsular polymer in which reducing groups can be generated by selective hydrolysis with retention of antigenic specificity. In the following non-limiting example, capsular polymer fragments were made from the Sp. 6 capsular polymer by selective acid hydrolysis and were conjugated to CRM$_{197}$. The product retained antigenic specificity for both the Sp capsular polymer and the CRM$_{197}$ component.

Generation of Reducing Fragments From Capsular Polymers (CP)

1. A sample of the CP of Sp. 6 (Danish type 6A, Eli Lilly Co.) was assayed for total hexose by the phenol-sulfuric acid method standardized with D-glucose and for reducing activity by the alkaline ferricyamide method also standardized with D-glucose.

2. A Pyrex tube received 3.3 mg Sp. 6 CP dissolved with 0.66 ml water. The sample was chilled to 0° C., 0.073 ml of 0.1N HCl were added, and the tube was sealed.

3. The tube was immersed 10 minutes in a boiling water bath, then rechilled to 0° C. A small sample was assayed for reducing activity as described in step 1:

| CP | Time heated at 100° C. | Total hexose/ reducing hexose |
|---|---|---|
| Sp. 6 | 0 minutes | >350 |
|  | 10 minutes | 6.5 |

4. The hydrolyzed preparation (minus the 2% used for assay) was lyophilized. The dried material was dissolved with 0.1 ml water, transferred to microcentrifuge tube, and lyophilized again.

Conjugation to $CRM_{197}$ 1. To the re-dried hydrolysate was added 0.004 ml of 2 M potassium phosphate buffer pH 8 and 1 mg of $CRM_{197}$ dissolved in 0.2 ml of 0.01M sodium phosphate buffer pH 7. The resulting mixture was lyophilized and resuspended with 0.05 ml water (estimated total volume 0.063 ml).

2. To the tube was added 0.007 ml of sodium cyanoborohydride at 200 mg/ml, and the preparation was incubated 18 days at 37° C.

3. 0.6 ml 80% saturated ammonium sulfate (SAS) was added.

4. The tube was incubated 1 hour at 0° C. and centrifuged 15 minutes at 8000 G; the supernate was removed.

5. The precipitate was washed by suspension in 0.6 ml of 80% SAS buffered at pH 8 with 0.01M sodium phosphate, followed by centrifugation 15 minutes at 8000 G.

6. The precipitate was suspended with 0.02 ml of 0.5M $Na_2HPO_4$ and 0.2 ml 9.5M urea.

7. 1 ml SAS was added, the precipitate was isolated as in step 4 and suspended in urea at about 8M as in step 6.

8. The suspension was centrifuged 15 minutes at 8000 G.

9. The supernate was separated and dialyzed against 0.01M sodium phosphate buffer pH 7 at 4° C.

10. The dialyzed preparations, designated $CRM_{197}$-Sp. 6 was assayed for the following:
protein by the Folin phenol reaction;
Sp antigenicity by inhibition of binding of antibody to radiolabeled Sp CP (as described for PRP in Table 3);
$CRM_{197}$ antigenicity by the inhibition of antibody binding to diphtheria toxoid (DT) (as described in step o of the description of $CRM_{197}$-PRP-S#2); and
anti-CP immunogenicity by inhibition of the binding of antibody to diphteria toxoid (DT) (as described in step p of the description of $CRM_{197}$-PRP-S#)

| Preparation | ng CP equivalance/ μg Protein | μg DT equivilance/ μg protein |
|---|---|---|
| $CRM_{197}$ Sp. 6 | 0.4 | 0.36 |

TABLE 10
ANTI-CP IMMUNOGENIC RESPONSE OF WEANLING RABBITS WITH CONTROLS AND CONJUGATES OF STREPTOCOCCUS PNEUMONIAE SEROTYPE 6 FRAGMENTS OF $CRM_{197}$

| Rabbit | Vaccinated With* | Percent $^{14}$C-CP Bound in Samples at age** | | | |
|---|---|---|---|---|---|
| | | 6 wk | 8 wk | 10 wk | 11 wk |
| 1 | Sp 6 CP, 25 μg | 6 | 6 | 7 | 7 |
| 2 | " | 6 | 13 | 13 | 11 |
| 3 | Sp 6 bacteria 25 μg | 4 | 10 | 12 | 16 |
| 4 | " | 8 | 12 | 22 | 21 |
| 5 | $CRM_{197}$ Sp 6, 25 μg | 4 | 6 | 30 | 49 |
| 6 | " | 4 | 8 | 30 | 54 |

*Injected subcutaneously just prior to taking serum samples. Serum samples were taken at age 6, 8 and 10 weeks.
**25 ul serum incubated with 2 nCi $^{14}$C-labelled CP.

I claim:

1. immunogenic conjugate comprising the reductve amination product of an immunogenic capsular polymer fragment having a chain length of from about 10 to about 30 monomeric units and a reducing end, which fragment is derived from the capsular polymer of a *Streptococcus pneumoniae* or *Haemophilus influenzae* bacterium, and a bacterial toxin or toxoid.

2. The immunogenic conjugate of claim 1, wherein the capsular polymer is immunogenic in mature humans and less immunogenic in infant humans.

3. The immunogenic conjugate of claim 1, wherein the reductive amination is performed in the persence of cyanoborohydride anions.

4. The immunogenic conjugate of claim 1, wherein the toxin or toxoid is diphtheria toxin or toxoid.

5. The immunogenic conjugate of claim 4, wherein the toxoid is $CRM_{197}$.

6. The immunogenic conjugate of claim 1, wherein the toxin or toxoid is tetanus toxin or toxoid.

7. The immunogenic conjugate of claim 1, wherein the toxin or toxoid is a pseudomonas toxin or toxoid.

8. The immunogenic conjugate of claim 1, wherein the toxin or toxiod is a staphylococcus toxin or toxoid.

9. The immunogenic conjugate of claim 1, wherein the toxin or toxoid is a streptococcus toxin or toxoid.

10. The immunogenic conjugate of claim 1, wherein the toxin or toxoid is pertussis toxin or toxoid.

11. The immunogenic conjugate of claim 1, wherein the toxin or toxoid is *Escherichia coli* toxin or toxoid.

12. The immunogenic conjugate of claim 1, wherein the bacterial pathogen is *Haemophilus influenzae* type b.

13. The immunogenic conjugate of claim 1, wherein the bacterial pathogen is *Streptococcus pneumoniae* serotype 3.

14. The immunogenic conjugate of claim 1, wherein the bacterial pathogen is *Streptococcus pneumoniae* serotype 6.

15. The immunogenic conjugate of claim 1, wherein the bacterial pathogen is *Streptococcus pneumoniae* serotype 12.

16. The immunogenic conjugate of claim 1, wherein the bacterial pathogen is *Streptococcus pneumoniae* serotype 14.

17. The immunogenic conjugate of claim 1, wherein the bacterial pathogen is *Streptococcus pneumoniae* serotype 19.

18. The immunogenic conjugate of claim 1, wherein the bacterial pathogen is *Streptococcus pneumoniae* serotype 23.

19. The immunogenic conjugate of claim 1, wherein the bacterial pathogen is *Streptococcus pneumoniae* serotype 51.

20. The immunogenic conjugate of claim 5, wherein the bacterial pathogen is *Haemophilis influenzae* type b.

21. The immunogenic conjugate of claim 5, wherein the bacterial pathogen is *Streptococcus pneumoniae* serotype 6.

22. The immunogenic conjugate of claim 5, wherein the bacterial pathogen is *Streptococcus pneumoniae* serotype 14.

23. The immunogenic conjugate of claim 5, wherein the bacterial pathogen is *Streptococcus pneumoniae* serotype 19.

24. The immunogenic conjugate of claim 5, wherein the bacterial pathogen is *Streptococcus pneumoniae* serotype 23.

25. The immunogenic conjugate of claim 1, wherein the fragment is derived from the capsular polymer by oxidative cleavage.

26. The immunogenic conjugate of claim 1, wherein the fragment is derived from the capsular polymer by periodate.

27. The immunogenic conjugate of claim 1, wherein the fragment is derived from the capsular polymer by hydrolysis of a glycosidic linkage.

28. The immunogenic conjugate of claim 27, wherein the hydrolysis is accomplished enzymatically.

29. The immunogenic conjugate of claim 27, wherein the hydrolysis is accomplished chemically.

30. The immunogenic conjugate of claim 27, wherein the hydrolysis is accomplished by acid.

31. The immunogenic conjugate of claim 12, wherein the fragment elutes on a column of Bio-Gel P-10 at a Ve/Vo ratio of $\leq 1.08$.

32. The immunogenic conjugate of claim 12, wherein the fragment elutes on a column of Bio-Gel P-10 at a Ve/Vo ratio of 1.09-1.38.

33. The immunogenic conjugate of claim 12, wherein the fragment elutes on a column of Bio-Gel P-10 at a Ve/Vo ratio of 1.39-1.99.

34. An immunogenic conjugate comprising a formalin treated reductive amination product of an immunogenic capsular polymer fragment having a chain length of from about 10 to about 30 monomeric units and a reducing end, which fragment is derived from the capsular polymer of a *Streptococcus pneumoniae* or *Haemophilus influenzae* bacterium, and a bacterial toxin or toxoid.

35. The immunogenic conjugate of claim 34, wherein the bacterial toxoid is diptheria toxoid.

36. The immunogenic conjugate of claim 35, wherein the Toxoid is $CRM_{197}$.

37. The immunogenic conjugate of claim 34, wherein the bacterial toxin or toxoid is tetanus toxin or toxoid.

38. An immunogenic conjugate of (1) a PRP polysaccharide fragment having reducing terminal groups derived from the capsular polysaccharide of *Haemophilus influenzae* type b by selective acidic hydrolysis of a portion of the ribosyl ribitol linkages therein and (2) the diphtheria toxin protein $CRM_{197}$.

39. The conjugate of claim 38 prepared by the reductive amination of the PRP fragment and protein.

40. The conjugate of claim 38 prepared by reductive amination in the presence of cyanoborohydride anions.

41. The conjugate of claim 38 wherein said PRP fragment elutes from a column of Bio-Gel P-10 at a Ve/Vo ratio of $\leq 1.08$.

42. The conjugate of claim 38 wherein said PRP fragment elutes from a column of Bio-Gel P-10 at a Ve/Vo ratio of 1.09-1.38.

43. The conjugate of claim 38 wherein said PRP fragment elutes from a column of Bio-Gel P-10 at a Ve/Vo ratio of 1.39-1.99.

44. The conjugate of claim 38 wherein said PRP fragment elutes from a column of Bio-Gel P-10 at a Ve/Vo ratio of 2.0-2.4.

45. A vaccine that elicits effective levels of anti-capsular polymer antibodies in humans, comprising: the immunogenic conjugate of claim 1.

46. A method for actively immunizing humans against a bacterial pathogen having a capsular polymer, comprising: administering an effective amount of the vaccine of claim 45.

47. A vaccine that elicits effective levels of anti-PRP antibody formations in young warm-blooded mammals comprising an immunogenic amount of the conjugate of claim 41 and a pharmaceutically acceptable carrier.

48. A vaccine that elicits effective levels anti-PRP antibody formations in young warm-blooded mammals comprising an immunogenic amount of the conjugate of claim 42 and a pharmaceutically acceptable carrier.

49. The immunogenic conjugate of claim 5, wherein the bacterial pathogen is *Streptoccoccus pneumoniae* serotype 3.

50. The immunogenic conjugate of claim 5, wherein the bacterial pathogen is *Streptococcus pneumoniae* serotype 51.

* * * * *